United States Patent [19]
Woodruff

[11] Patent Number: 5,153,191
[45] Date of Patent: Oct. 6, 1992

[54] CHOLECYSTOKININ ANTAGONISTS USEFUL FOR TREATING DEPRESSION

[75] Inventor: Geoffrey N. Woodruff, Braughing, United Kingdom

[73] Assignee: Warner-Lambert Company, Morris Plains, N.J.

[21] Appl. No.: 747,814

[22] Filed: Aug. 20, 1991

[51] Int. Cl.$^5$ .................. A61K 31/55; A61K 31/675; A61K 31/535; A61K 31/44
[52] U.S. Cl. ...................... 514/221; 514/80; 514/237.5; 514/330; 514/404; 514/563
[58] Field of Search ............ 514/221, 231.2, 315, 514/563, 404, 80, 210, 330, 237.5

[56] References Cited

U.S. PATENT DOCUMENTS 4,791,215 12/1988 Rovati et al. .............. 558/415
4,820,834 4/1989 Evans et al. .............. 540/504

FOREIGN PATENT DOCUMENTS 0405537 6/1990 European Pat. Off. .............. 209/20

OTHER PUBLICATIONS

*The Merck Manual*, 14th ed. (1982) pp. 1448-1462.
*Ann. Rev. Pharmacol. Toxicol.*, 1991, 31: 469-501, G. N. Woodruff et al., "Cholecystokinin Antagonists".
*J. Med. Chem.*, 1991, 34, 1505-1508, M. J. Yu et al., "Quinazolinone Cholecystokinin-B Receptor Ligands".

*Primary Examiner*—Frederick E. Waddell
*Assistant Examiner*—Raymond J. Henley, III
*Attorney, Agent, or Firm*—Elizabeth M. Anderson

[57] ABSTRACT

The invention concerns cholecystokinin antagonists useful in the treatment major and minor forms of depression. Especially useful are $CCK_A$ antagonists such as devazepide and $CCK_B$ antagonists such as L-365,260 and LY262691.

9 Claims, No Drawings

CHOLECYSTOKININ ANTAGONISTS USEFUL FOR TREATING DEPRESSION

BACKGROUND OF THE INVENTION

Cholecystokinin (CCK) is a neuropeptide with a widespread distribution in brain. CCK receptors are classified into two types; $CCK_A$ and $CCK_B$, both of which are present in brain (Woodruff, G. N. and Hughes, J., 1991, *Ann. Rev. Pharmacol.* 31, 469-501).

Devazepide is a selective antagonist of $CCK_A$ receptors. The chemical name and structure of devazepide are:

1H-indole-2-carboxamide, N-(2,3-dihydro-1-methyl-2-oxo-5-phenyl-1H-1,4-benzodiazepin-3-yl)-, or (L 364718) and

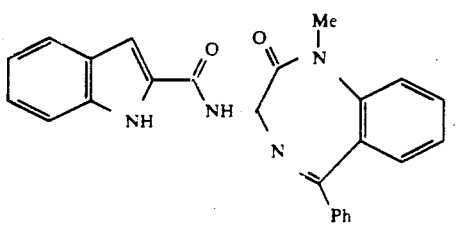

L-365,260 is a selective antagonist of $CCK_B$ receptors. The chemical name and structure of L-365,260 is (R)-N-(2,3-dihydro-1-methyl-2-oxo-5-phenyl-1H-1,4-benzodiazepine-3-yl)-N'-(3-methylphenyl)urea and

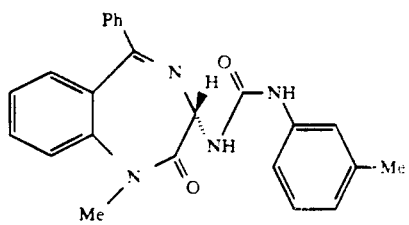

Other CCK antagonists are lorglumide and loxiglumide. Lorglumide is DL-4-(3,4-dichlorobenzoylamino)-5-(dipentylamino)-5-oxopentanoic acid and loxiglumide is (±)-4-[(3,4-dichlorobenzoyl)amino]-5-[(3-methoxyproxyl)pentylamino]-5-oxo-pentanoic acid.

These $CCK_A$ and $CCK_B$ antagonists are described in U.S. Pat. No. 4,791,215 and U.S. Pat. No. 4,820,834. These documents are hereby incorporated by reference.

The above patents cover compounds of the instant invention, methods for preparing them, and several uses thereof.

The uses disclosed are gastric acid secretion disorders, gastrointestinal motility, pancreatic secretions, dopaminergic functions, analgesics, psychic disturbances, anorexia, weight increases in farm animals, and pathological cellular growth such as tumors.

Other CCK antagonists include compounds (*J. Med. Chem.* 1991, 34, 1505-8) of formula

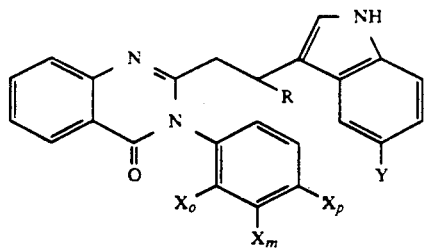

or a pharmaceutically acceptable salt thereof wherein
$X_o$ is hydrogen, fluorine, chlorine, methoxy, or trifluoromethyl;
$X_m$ is hydrogen, fluorine, chlorine, bromine, methyl, ethyl, methoxy, propoxy, trifluoromethyl, cyclopentyloxy, MeS, or $NMe_2$;
$X_p$ is hydrogen, fluorine, chlorine, bromine, methoxy, or $X_m$ and $X_p$ together form $-OCH_2O-$;
Y is hydrogen, fluorine, bromine, chlorine, or methoxy; and
R is hydrogen or methyl.

These CCK-B receptor ligands are also useful as agents in the treatment of depression.

Other compounds (presented at the 23rd Central 24th Great Lakes Joint Regional American Chemical Society Meeting; Abstract No. 306) useful in treating depression are those of formula

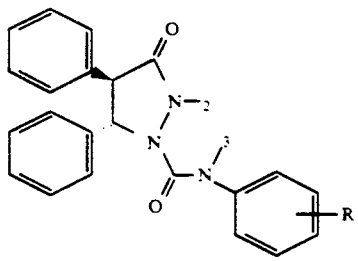

or a pharmaceutically acceptable salt thereof,
wherein R is 2,3-dichloro, hydrogen, 4-trifluoromethyl, 4-chloro, 4-bromo, 4-methyl, 4-ethyl, 4-isopropyl, 4-methoxy, 4-$OCH_2Ph$, 3-trifluoromethyl, 3-methyl, 3-methoxy, 3-trifluoromethyl, 4-chloro, 3,4-dichloro, 3,4-$(CH_2)_3$, 3,4-$(CH_2)_4$, 2-trifluoromethyl;
$R_2$ is hydrogen or methyl; and
$R_3$ is hydrogen or methyl.

Other compounds useful for treating depression are those of formula

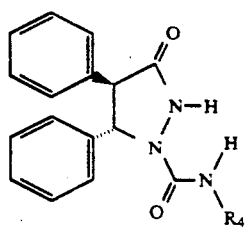

or a pharmaceutically acceptable salt thereof wherein $R^4$ is 3-pyridyl, 4-pyridyl, 1-naphthyl, 2-naphthyl, 3-quinolinyl, 6-quinolinyl, n-Bu, c-hexyl, $CH_2Ph$, $CH_2Ph$-3,4-diCl, $(CH_2)_2Ph$, $(CH_2)_2Ph$-2-Cl, or $(CH_2)_3Ph$.

Other compounds useful for treating depression are those of formula

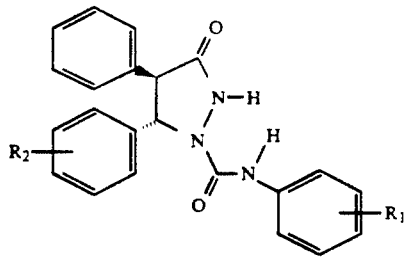

IV or a pharmaceutically acceptable salt thereof wherein
$R^1$ is 4-trifluoromethyl or 4-bromo;
$R^2$ is hydrogen, 2-chloro, 3-cyano, 3-methoxy, 4-N(Me)$_2$, 2-methoxy, 2,3-dichloro, 3-CONH$_2$, 4-NO$_2$;
$R^3$ is hydrogen, 2-chloro, 3-chloro, 4-chloro, 3-methoxy, or 4-methoxy.

Especially useful are compounds of formula IV wherein $R^1$ is 4-CF$_3$, $R^2$ is 2-Cl, and $R^3$ is hydrogen and wherein $R^1$ is 4-Br, $R^2$ is 2-Cl, and $R^3$ is 2-Cl.

Other compounds useful in treating depression are those of formula

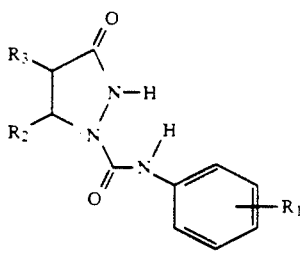

V or a pharmaceutically acceptable salt thereof wherein
$R^1$ is 4-bromo or 4-trifluoromethyl;
$R^2$ is phenyl, 3-pyridyl, or n-butyl; and
$R^3$ is 1-naphthyl, phenyl, or n-butyl.

Other compounds useful in treating depression are those of formula

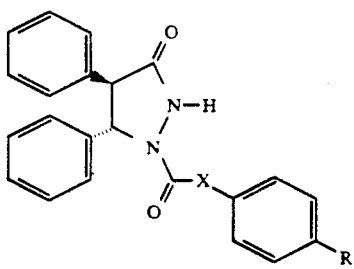

VI or a pharmaceutically acceptable salt thereof wherein
X is absent, CH$_2$, oxygen, or sulfur, and R is trifluoromethyl, bromine, or chlorine.

Other compound useful are selected from:

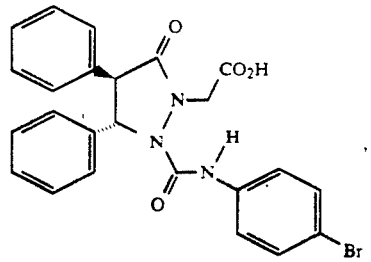

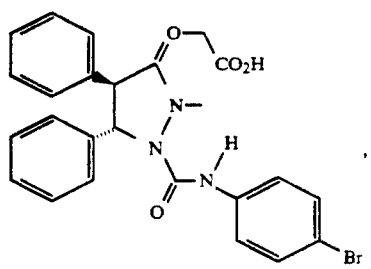

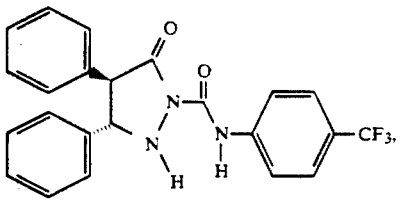

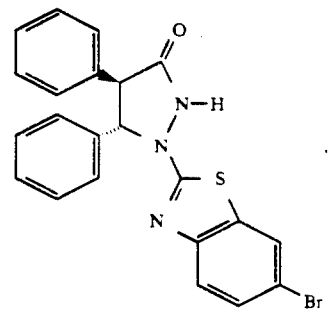

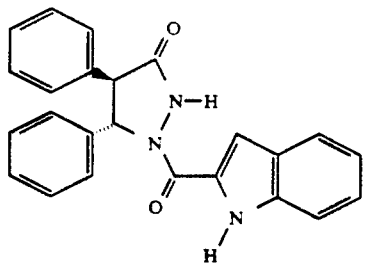

or a pharmaceutically acceptable salt thereof.
Especially useful as agents for depression are CCK antagonists
1-pyrazolidinecarboxamide, N-(4-bromophenyl)-3-oxo-4,5-diphenyl-, trans-,
1-pyrazolidinecarboxamide, 5-(2-chlorophenyl)-3-oxo-4-phenyl-N-[4-trifluoromethyl)phenyl]-, trans-, and
1-pyrazolidinecarboxamide, N-(4-bromophenyl)-5-(2-chlorophenyl)-3-oxo-4-phenyl-, trans-.
The above references do not disclose the use of CCK antagonists for treating depression.

Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the diagnostic and Statistical Manual of Mental Disorders (Third Edition Revised) referred to as the DSM-III-R manual published by the American Psychiatric Association, 1987.

The compounds of the instant invention have an antidepressant action in patients with major and minor forms of depression.

SUMMARY OF THE INVENTION

The present invention relates to a novel therapeutic use of known compounds, $CCK_A$ and $CCK_B$ antagonists, their derivatives and pharmaceutically acceptable salts. The present invention concerns a method for treating depression in a mammal in need of such treatment.

The treatment comprises administering in unit dosage form an amount effective to treat depression of a $CCK_A$ or $CCK_B$ antagonist or a pharmaceutically acceptable salt thereof to a mammal in need of such treatment.

Preferred compounds include but are not limited to $CCK_A$ antagonists devazepide, lorglumide, and loxiglumide.

Preferred compounds include but are not limited to $CCK_B$ antagonist L-365,260 and LY262691.

Pharmaceutical compositions of a compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma, propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primary liquid composition. The more satisfactory compositions are those in which a much higher proportion of the active ingredient is present.

Routes of administration of a subject compound or its salts are oral or parenteral. For example, a useful intravenous dose is between 100 and 800 mg and a useful oral dosage is between 200 and 800 mg.

A unit dosage form of the instant invention may also comprise other compounds useful in the therapy of depression.

A typical dose is, for example, from 600 to 2400 mg per day given in three individual doses.

Useful individual doses are from 5 mg to 50 mg parenterally or from 5 mg to 600 mg enterally or a compound or a pharmaceutically acceptable salt thereof.

A skilled physician will be able to determine the appropriate situation in which subjects are susceptible to or at risk of minor or major depression for administration by methods of the present invention.

DETAILED DESCRIPTION

The present invention relates to a method of treating depression which comprises administering a therapeutically effective amount of at least one compound or a pharmaceutically acceptable salt thereof of D,L-glutamic acid and D,L-aspartic acid of formulae:

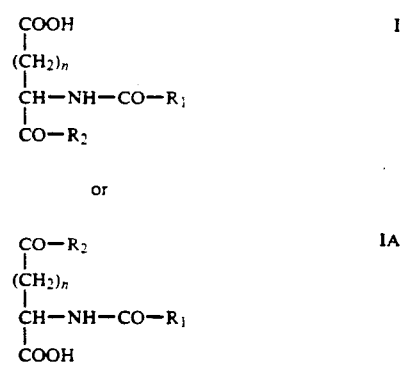

wherein n is 1 or 2

$R_1$ is a phenyl group mono-, di-, or tri-substituted with linear or branched $C_1$-$C_4$ groups, which may be the same or different, or with halogens, with a cyano group or with a trifluoromethyl group;

$R_2$ is selected from the group consisting of morpholino, piperidino, and amino with one or two linear, branched, or cyclic alkyl group substituents containing from 1 to 8 carbon atoms which may be the same or different.

The present invention also relates to a method of treating depression which comprises administering a therapeutically effective amount of at least one compound or a pharmaceutically acceptable salt of a compound of formula

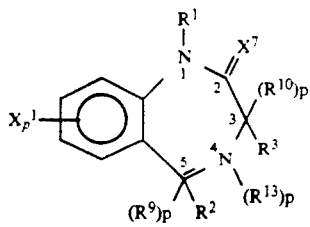

wherein
$R^1$ is H, $C_1$-$C_6$ linear or branched alkyl, loweralkenyl, lower alkynyl, $-X^{12}COOR^6$, $-X^{11}$cycloloweralkyl, $-X^{12}NR^4R^5$, $X^{12}CONR^4R^5$, $-X^{12}CN$, or $-X^{11}CX_3^{10}$;

$R^2$ is H, loweralkyl, substituted or unsubstituted phenyl (wherein the substituents may be 1 or 2 of halo, loweralkyl, loweralkoxy, loweralkylthio, carboxyl, carboxyloweralkyl, nitro, -$CF_3$, or hydroxy), 2-, 3-, 4-pyridyl,

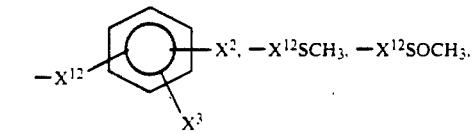

$-X^{12}SO_2CH_3$, or $-X_{12}COOR^6$; $R^3$ is $-X^{11}R^7$, $-X^{11}\overset{OH}{\underset{|}{C}}HR^7$, $-X^{11}-\overset{OH}{\underset{R_a^7}{\overset{|}{C}}}-R^7$, $-X^{11}\overset{O}{\overset{\|}{C}}R^7$, $-X^{11}NR^{18}(CH_2)_qR^7$, $-X^{11}NR^{18}\overset{R^7}{\underset{|}{\overset{(CH_2)_q}{\underset{|}{C}H}}}COOR^6$, $-X^{11}X^9\overset{O}{\overset{\|}{C}}(X^{11})R^7$, $-X^{11}\overset{O}{\overset{\|}{C}}X^9X^{11}R^7$, $-NH(CH_2)_{2-3}NHR^7$, $-NH(CH_2)_{2-3}NHCOR^7$ $-X^{11}X^9\overset{O}{\overset{\|}{C}}CHCH_2R^7$, $-X^{11}X^9\overset{O}{\overset{\|}{C}}X_a^9(X^{11})R^7$, $-X^{11}X^9\overset{O}{\overset{\|}{C}}-\overset{NH_2}{\underset{|}{C}H}-CH_2R^7$, $-X^{11}X^9\overset{O}{\overset{\|}{C}}(CH_2)_qX_a^9$-[phenyl-$X^2$, $X^3$]

$-X-^{11}NR^{18}SO_2(CH_2)_qR^7$ or $=\overset{H}{\underset{|}{C}}-R_7$ wherein
$R_4$ and $R_5$ are independently $R^6$ or in combination with the N of the $NR^4R^5$ group form an unsubstituted or mono or disubstituted, saturated or unsaturated, 4-7 membered heterocyclic ring or benzofused 4-7 membered heterocyclic ring, or said heterocyclic ring or said benzofused heterocyclic ring which further comprises a second heteroatom selected from O and $NCH_3$ and the substituent(s) is/are independently selected from $C_{1-4}$ alkyl;

$R^6$ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or $CF_3$;

$R_7$ and $R_a^7$ are independently α- or β-naphthyl, substituted or unsubstituted phenyl (wherein the substituents may be 1 or 2 of halo, $-NO_2$, $-OH$, $-X^{11}R^4R^5$, loweralkyl, $CF_3$, CN, $SCF_3$, C≡CH, $CH_2SCF_3$,

$OCHF_2$, SH, SPh, $PO_3H$-loweralkoxy, or loweralkylthio, COOH), 2-, 3-, 4-pyridyl,

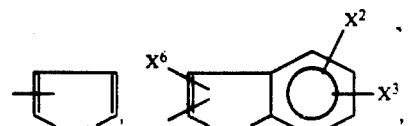

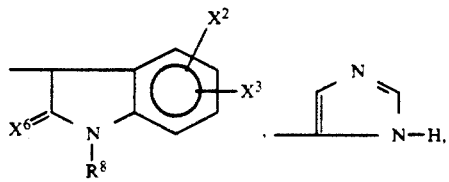

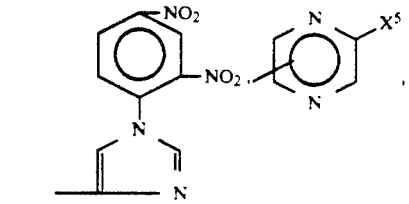

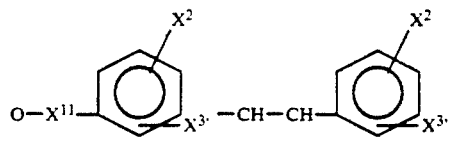

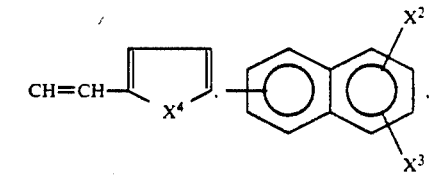

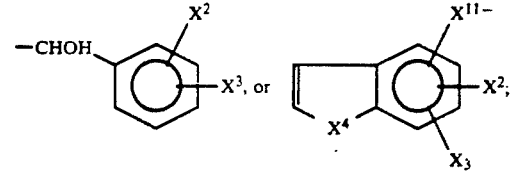

$R^8$ is H, loweralkyl, cycloloweralkyl, $-X^{12}CONH_2$, $-X^{12}COOR^6$, $-X^{12}$-cycloloweralkyl, $-X^{12}NR^4R^5$,

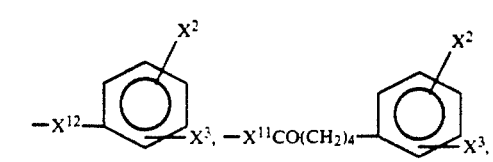

-continued

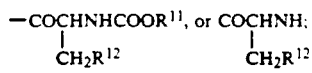

$R^9$ and $R^{10}$ are independently H, —OH, or —CH$_3$;
$R^{11}$ and $R^{12}$ are independently loweralkyl or cyclo-loweralkyl;
$R^{13}$ is H, loweralkyl, acyl, O, or cycloloweralkyl;
$R^{14}$ is loweralkyl or phenylloweralkyl;
$R^{15}$ is H, loweralkyl,

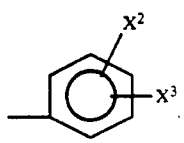

or —NH$_2$;
$R^{18}$ is H, loweralkyl, or acyl;
p is 0 when its adjacent === is unsaturated and 1 when its adjacent === is saturated except that when $R^{13}$ is O, p=1, and is unsaturated;
q is 0 to 4;
r is 1 or 2;
$X^1$ is H, —NO$_2$, CF$_3$, CN, OH, loweralkyl, halo, loweralkylthio, loweralkoxy, —, $X^{11}$COOR$^6$, or —$X^{11}$NR$^4$R$^5$—;
$X^2$ and $X^3$ are independently H, —OH, —NO$_2$, halo, loweralkylthio, loweralkyl, or loweralkoxy;
$X^4$ is S, O, CH$_2$, or NR$^{18}$ or NR$^8$;
$X^5$ is H, CF$_3$, CN, —COOR$^6$, NO$_2$I, or halo;
$X^6$ is O or HH,
$X^7$ is O, S, HH, or NR$^{15}$;
$X^8$ is H, loweralkyl;
$X^9$ and $X_a^9$ are independently NR$^{18}$ or O;
$X^{10}$ is F, Cl, or Br;
$X^{11}$ is absent or C$_{1-4}$ linear or branched alkylidene;
$X^{12}$ is C$_{1-4}$ linear or branched alkylidene;
—is a saturated or unsaturated bond; or

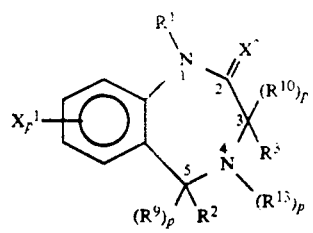 III wherein $R^1$, $R^2$, $R^4$, $R^5$, $R^6$, $R^8$, $R^9$, $R^{10}$, $R^{11}$, $R^{12}$, $R^{13}$, $R^{14}$, $R^{15}$, p, q, r, $X^1$, $X^2$, $X^3$, $X^5$, $X^6$, $X^7$, $X^8$, $X^9$, $X^{10}$, $X^{11}$, and $X^{12}$ are as defined above.

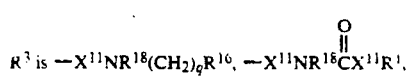

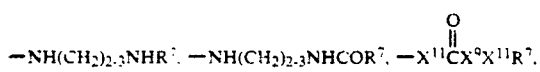

-continued

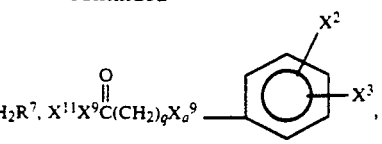

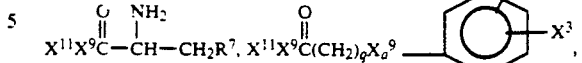

$R^7$ is α- or β-naphthyl, substituted or unsubstituted phenyl (wherein the substituents may be 1 to 2 of halo, —NO$_2$, —OH, —$X^{11}$NR$^4$R$^5$, loweralkyl, CF$_3$, CN, SCF$_3$, C≡CH, CH$_2$SCF$_3$,

OCHF$_2$, SH, SPh, PO$_3$H, loweralkoxy, loweralkylthio, or COOH), 2-, 3-, 4-pyridyl;

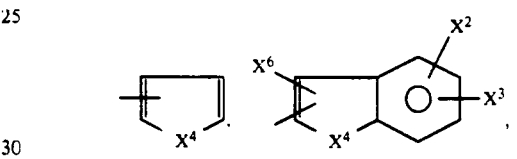

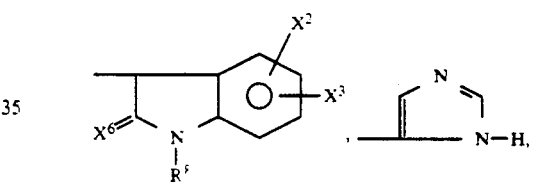

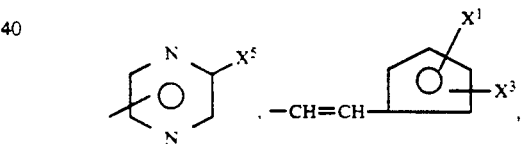

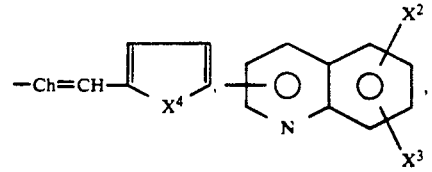

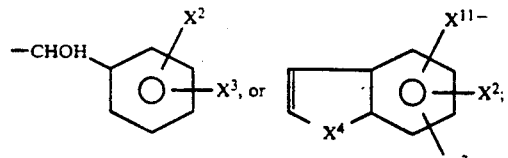

$R^{16}$ is alpha or beta naphthyl or 2-indolyl;
$R^{18}$ is H or loweralkyl; and
= is a saturated or unsaturated bond.

Certain CCK$_A$ and CCK$_B$ antagonists were tested in the Porsolt test, an animal model of depression, and in the "open field test" in the olfactory bulbectomised rat model of depression.

Methods

1. Porsolt Test (Behavioral Despair)

This test is based on the original method of Porsolt, et al (1977), Porsolt, R. D., La Pichon, M., and Jalpe, M. Depression: a new animal model sensitive to antidepressant treatment, *Nature* 266:730-732. On the first day of the experiment, the rats were plunged individually into a container 40 cm high, 18 cm diameter containing 15 cm of water at a temperature of 25° C. The animals were left to swim in the water for 15 minutes before being removed, allowed to dry, and returned to their home cage. Twenty-four hours later the procedure was repeated but on this occasion the duration that the rats remained immobile in a 5-minute observation period was recorded.

Animals received their first dose 15 minutes after removal from the water on the first day. They received the second dose 1 hour prior to the second placement in the water. Experiments were carried out in olfactory bulbectomised and in nonoperated animals.

Standard antidepressants such as desipramine caused a significant reduction in immobility in this test.

Results

1. Porsolt Test (Behavioral Despair)

The results obtained are shown in Table 1 below.

TABLE 1

| Group | | Time Immobile(s) |
|---|---|---|
| Vehicle | Median | 159 |
| (n = 8) | ST DEV | 54 |
| | Q1-Q3 | 151-239 |
| Devazepide | Median | 100* |
| (n = 8) | ST DEV | 38 |
| 0.1 mg/kg) | Q1-Q3 | 77-144 |

ST DEV = Standard Deviation
Q1-Q3 = Interquartile range
*P <0.005 ⎫
***P < 0.001 ⎭ Mann Whitney U Test Table 1 shows the effect of devazepide in the Porsolt test in nonoperated animals. Devazepide (0.5 mg/kg) caused a significant decrease in immobility, indicating antidepressant activity.

2. Open Field Test in Olfactory Bulbectomised Animals

This apparatus is essentially as described by Gray & Lalljee, Gray, J. A. and Lalljee, B. (1974): Sex differences in emotional behavior in the rat: correlation between the 'open field' defecation and active avoidance. *Anim. Behav.* 22: 856-861. The open field consisted of a circular base, 90 cm in diameter which was divided into 10 cm squares by faint yellow lines. The wall surrounding the base consisted of a 75 cm high aluminum sheet. Illumination was provided by a 60 watt bulb, positioned 90 cm above the floor of the apparatus. All measurements were carried out in a darkened room in the morning. Each animal was placed in the center of the open field apparatus and the following parameters were measured over a 3 minute period:

a) Ambulation: the number of squares crossed;

b) Rearing: the number of times the rat simultaneously raised both forepaws off the floor of the apparatus;

c) Grooming: the number of times the rat stopped and groomed itself; and d) Defecation: the number of fecal boli deposited.

Experiments were carried out in sham operated rats and in rats with olfactory bulbectomy performed as described by Cairncross, K. D., Wren, A. F., Cox, B., and Schrieden, H. (1977): Effects of olfactory bulbectomy and domicile on stress induced corticosteroid release in the rat, *Physiol. Behav.* 19:4845-487.

Since the $CCK_A$ antagonist, art recognized devazepide, demonstrated activity in the recognized behavioral despair model, $CCK_A$ receptor antagonists will be effective in the treatment of depression in man.

$CCK_B$ antagonists are also effective in the treatment of depression in man.

Scheme I below illustrates a method for preparing the above compounds.

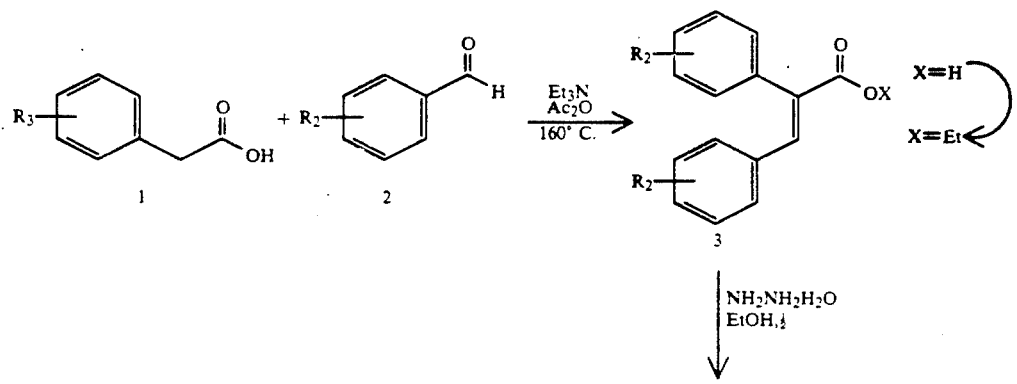

SCHEME 2

SCHEME 2 -continued

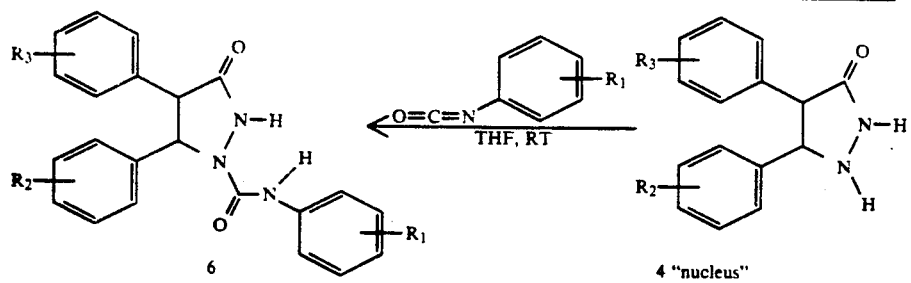

Compounds 1 and 2 are commercially available. They are reacted at 160° C. in ET$_3$N and Ac$_2$O to produce an acid of formula 3. The acid is dissolved in methanol. HCl is bubbled through the reaction mixture for about 10 minutes. This is then stirred at reflux for several hours. HCl is again bubbled through the reaction mixture. This is stirred at reflux overnight. This is then concentrated in a vacuum and the residue taken up in ether, washed with water, NaHCO$_3$ and brine, dried over MgSO$_4$, and concentrated in a vacuum to produce an ester of formula 3. This is mixed and stirred with NH$_2$NH$_2$.H$_2$O at reflux for 24 hours and then cooled. Water is added slowly until a solid begins to separate; about 400 mL of H$_2$O are added. Cool in an ice bath, filter, and wash to produce a compound of formula 4.

A desired compound of formula 4 is then mixed and stirred with a compound of formula 5 at room temperature overnight. Then it is concentrated in a vacuum. A compound of formula 6 is produced.

Such final products are, for example, 1-pyrazolidinecarboxamide, N-(4-bromophenyl)-3-oxo-4,5-diphenyl-, trans-, 1-pyrazolidinecarboxamide, 5-(2-chlorophenyl)-3-oxo-4-phenyl-N-[4-trifluoromethyl)phenyl]-, trans-, and 1-pyrazolidinecarboxamide, N-(4-bromophenyl)-5-(2-chlorophenyl)-3-oxo-4-phenyl-, trans-.

Examples of formulations of the subject compounds and of salts thereof are illustrated by the following.

EXAMPLE 1

Injectables 1 mg to 100 mg/mL

Devazepide for Injection USP q.s

The compound or a suitable salt thereof is dissolved in, for example, ethanol, and passed through a 0.2-micron filter. Aliquots of the filtered solution are added to ampoules or vials, sealed and sterilized.

EXAMPLE 2

Capsules 5 mg, 100 mg, 200 mg, 300 mg or 400 mg

Devazepide, 250 g

Lactose USP, Anhydrous q.s. or 250 g

Sterotex Powder HM, 5 g

Combine the compound and the lactose in a tumble blend for 2 minutes, blend for 1 minute with the intensifier bar, and then tumble blend again for 1 minute. A portion of the blend is then mixed with the Sterotex Powder, passed through a #30 screen, and added back to the remainder of the blend. The mixed ingredients are then blended for 1 minute, blended with the intensifier bar for 30 seconds, and tumble blended for an additional minute. The appropriately sized capsules are filled with 141 mg, 352.5 mg, or 705 mg of the blend, respectively, for the 50 mg, 125 mg, and 250 mg containing capsules.

EXAMPLE 3

Tablets 50 mg, 100 mg, 200 mg, 300 mg, 400 mg, 500 mg or 600 mg

Devazepide

Corn Starch NF, 200 g

Cellulose, Microcrystalline, 46 g

Sterotex Powder HM, 4 g

Purified Water q.s. or 300 mL

Combine the corn starch, the cellulose, and the compound together in a planetary mixer and mix for 2 minutes. Add the water to this combination and mix for 1 minute. The resulting mix is spread on trays and dried in a hot air oven at 50° C. until a moisture level of 1 to 2 percent is obtained. The dried mix is then milled with a Fitzmill through a #RH2B screen, and added back to the milling mixture and th total blended for 5 minutes by drum rolling. Compressed tablets of 150 mg, 375 mg, and 750 mg, respectively, of the total mix are formed with appropriate sized punches the 50 mg, 125 mg, or 500 mg containing tablets.

L-365,260 could also, for example, be used in Examples 1 to 3 above.

I claim:

1. A method for the treatment of idiopathic depression which comprises administering to a mammal in need of such treatment a therapeutically effective amount of a cholecystokinin antagonist or a pharmaceutically acceptable salt thereof in unit dosage form of formula

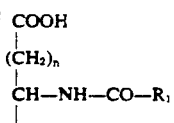   I or

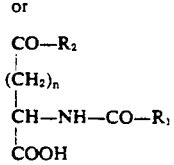   IA wherein n is 1 or 2

R$_1$ is a phenyl group mono-, di-, or tri-substituted with linear or branched $C_1$-$C_4$ groups, which may be the same or different, or with halogens, with a cyano group or with a trifluoromethyl group;

$R_2$ is selected from the group consisting of morpholino, piperidino, and amino with one or two linear, branched, or cyclic alkyl group substituents containing from 1 to 8 carbon atoms which may be the same or different.

2. A method according to claim 1 wherein the cholecystokinin antagonist is a lorglumide or loxiglumide or a pharmaceutically acceptable salt thereof.

3. A method according to claim 1 wherein an individual dose of 5 mg to 50 mg parenterally or of 5 mg to 600 mg enterally of the compound or a pharmaceutically acceptable salt thereof is administered.

4. A method for the treatment of idiopathic depression which comprises administering to a mammal in need of such treatment a therapeutically effective amount of a cholecystokinin antagonist or a pharmaceutically acceptable salt thereof in unit dosage form of formula

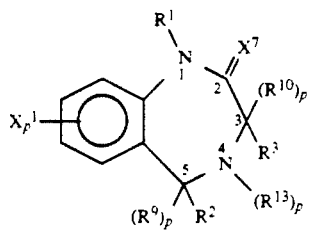
II wherein $R^1$ is H, $C_1$-$C_6$ linear or branched alkyl, loweralkenyl, lower alkynyl, $-X^{12}COOR^6$, $-X^{11}$cycloloweralkyl, $-X^{12}NR^4R^5$, $X^{12}CONR^4R^5$, $-X^{12}CN$, or $-X^{11}CX_3^{10}$;

$R^2$ is H, loweralkyl, substituted or unsubstituted phenyl wherein the substituents may be 1 or 2 of halo, loweralkyl, loweralkoxy, loweralkylthio, carboxyl, carboxyloweralkyl, nitro, $-CF_3$, or hydroxy), 2-, 3-, 4-pyridyl,

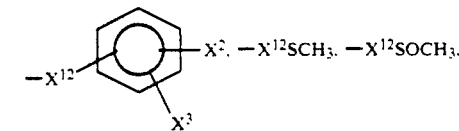

$-X^{12}SO_2CH_3$, or $-X^{12}COOR^6$; $R^3$ is $-X^{11}R^7$, $-X^{11}CHR^7$,

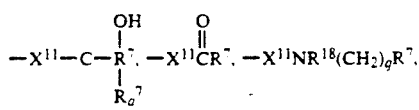

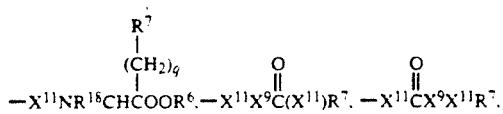

$-NH(CH_2)_{2-3}NHR^7$, $-NH(CH_2)_{2-3}NHCOR^7$

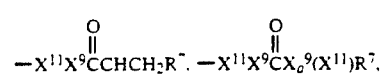

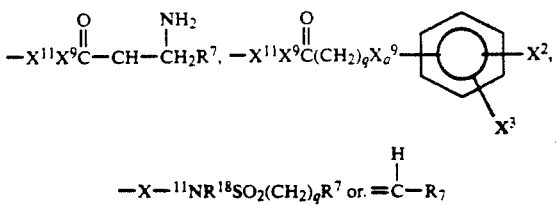

$-X-^{11}NR^{18}SO_2(CH_2)_qR^7$ or, $=\overset{H}{\underset{|}{C}}-R_7$ wherein $R_4$ and $R_5$ are independently $R^6$ or in combination with the N of the $NR^4R^5$ group form an unsubstituted or mono or disubstituted, saturated or unsaturated, 4–7 membered heterocyclic ring, or benzofused 4–7 membered heterocyclic ring, or said heterocyclic ring or said benzofused heterocyclic ring which further comprises a second heteroatom selected from O and $NCH_3$ and the substituent(s) is/are independently selected from $C_{1-4}$ alkyl;

$R^6$ is H, loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or $CF_3$;

$R_7$ and $R_a^7$ are independently α- or β-naphthyl, substituted or unsubstituted phenyl wherein the substituents may be 1 or 2 of halo, $-NO_2$, $-OH$, $-X^{11}R^4R^5$, loweralkyl, $CF_3$, $CN$, $SCF_3$, C©CH, $CH_2SCF_3$,

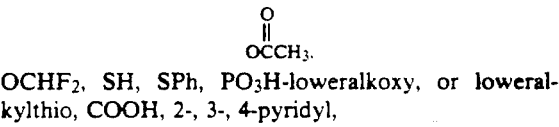

$OCHF_2$, $SH$, $SPh$, $PO_3H$-loweralkoxy, or loweralkylthio, $COOH$, 2-, 3-, 4-pyridyl,

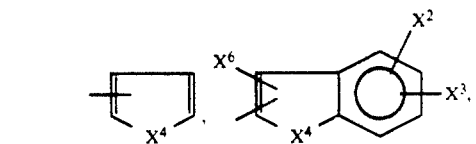

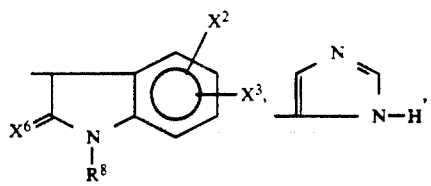

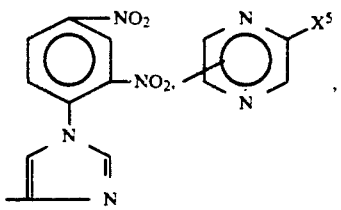

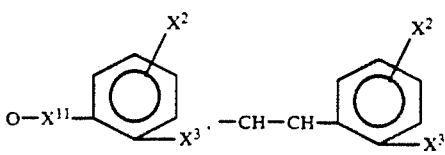

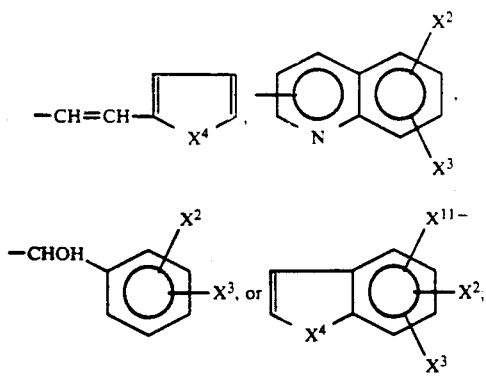

R[8] is H, loweralkyl, cycloloweralkyl, —X[12]CONH$_2$, —X[12]COOR[6], —X[12]-cycloloweralkyl, —X[12]NR[4]R[5],

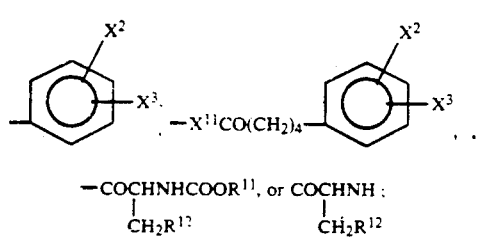

—COCHNHCOOR[11], or COCHNH ;
     |                        |
     CH$_2$R[12]              CH$_2$R[12]

R[9] and R[10] are independently H, —OH, or —CH$_3$;
R[11] and R[12] are independently loweralkyl or cycloloweralkyl;
R[13] is H, loweralkyl, acyl, O, cycloloweralkyl;
R[14] is loweralkyl or phenylloweralkyl;
R[15] is H, loweralkyl.

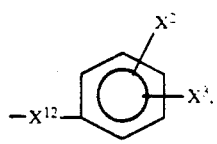

or —NH$_2$;
R[18] is H, loweralkyl, or acyl;
p is 0 when its adjacent═is unsaturated and 1 when its adjacent═is saturated except that when R[13] is O, p=1, and═is unsaturated;
q is 0 to 4;
r is 1 or 2;
X[1] is H, —NO$_2$, CF$_3$, CN, OH, loweralkyl, halo, loweralkylthio, loweralkoxy, —X[11]COOR[6], or —X[11]NR[4]R[5]—;
X[2] and X[3] are independently H, —OH, —NO[2], halo, loweralkylthio, loweralkyl, or loweralkoxy;
X[4] is S, O, CH$_2$, or NR[18] or NR[8];
X[5] is H, CF$_3$, CN, —COOR[6], NO$_2$, or halo;
X[6] is O or HH;
X[7] is O, S, HH, or NR[15];
X[8] is H, loweralkyl;
X[9] and X$_a$[9] are independently NR[18] or O;
X[10] is F, Cl, or Br;
X[11] is absent or C$_{1-4}$ linear or branched alkylidene;
X[12] is C$_{1-4}$ linear or branched alkylidene;
═ is a saturated or unsaturated bond; or

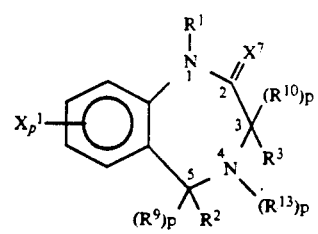

wherein R[1], R[2], R[4], R[5], R[6], R[8], R[9], R[10], R[11], R[12], R[13], R[14], R[15], p, q, r, X[1], X[2], X[3], X[5], X[6], X[7], X[8], X[9], X[10], X[11], and X[12] are as defined above, $$R^3 \text{ is } -X^{11}NR^{18}(CH_2)_qR^{16}, -X^{11}NR^{18}\overset{O}{\overset{\|}{C}}X^{11}R^7,$$

—NH(CH$_2$)$_{2-3}$NHR[7], —NH(CH$_2$)$_{2-3}$NHCOR[7], $$-X^{11}\overset{O}{\overset{\|}{C}}X^9X^{11}R^7, -X^{11}X^9\overset{O}{\overset{\|}{C}}CHCH_2R^7, -X^{11}NR^{18}\overset{O}{\overset{\|}{C}}X_a^9X^{11}R^7,$$
$$\underset{NHCOOR^{14}}{}$$

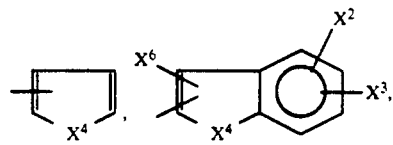

$$X^{11}NR^{18}SO_2(CH_2)_6R^7 \text{ or } X^{11}\overset{O}{\overset{\|}{C}}R^7;$$

R[7] is α-naphthyl, substituted or unsubstituted phenyl wherein the substituents may be 1 or 2 of halo, —NO[2], —OH, —X[11]NR[4]R[5], loweralkyl, CF$_3$, CN, SCF$_3$, C≡CH, CH$_2$SCF$_3$, $$\overset{O}{\overset{\|}{O}CCH_3},$$

OCHF$_2$, SH, SPh, PO$_3$H, loweralkoxy, loweralkylthio, or COOH, 2-, 3-, 4-pyridyl;

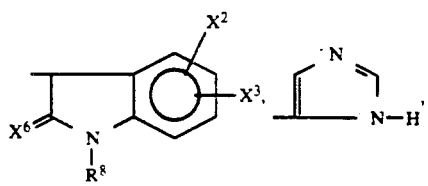

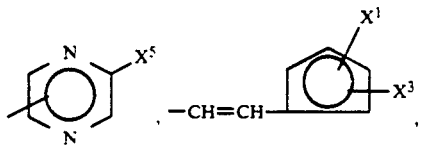

-continued

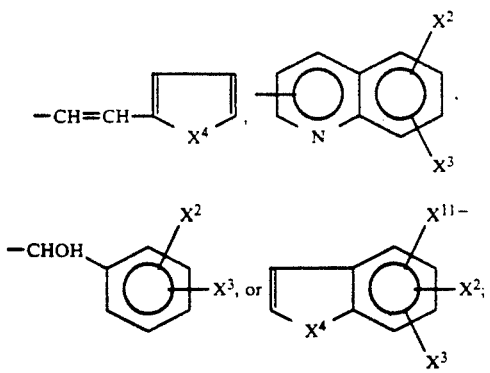

$R^{16}$ is alpha or beta naphthyl or 2-indolyl;
$R^{18}$ is H or loweralkyl; and
= is a saturated or unsaturated bond.

5. A method according to claim 4 wherein the cholecystokinin antagonist is (R)-N-(2,3-dihydro-1-methyl-2-oxo-5-phenyl-1H-1,4-benzodiazepine-3-yl)-N'-(3-methylphenyl)urea or a pharmaceutically acceptable salt thereof.

6. A method according to claim 4 wherein the cholecystokinin antagonist is devazepide or a pharmaceutically acceptable salt thereof.

7. A method according to claim 4 wherein an individual dose of 5 mg to 50 mg parenterally or of 5 mg to 600 mg enterally of the compound or a pharmaceutically acceptable salt thereof is administered.

8. A method for the treatment of idiopathic depression which comprises administering to a mammal in need of such treatment a therapeutically effective amount of a cholecystokinin antagonist or a pharmaceutically acceptable salt thereof in unit dosage form selected from 1-pyrazolidinecarboxamide, N-(4-bromophenyl)-3-oxo-4,5-diphenyl-, trans-; 1-pyrazolidinecarboxamide, 5-(2-chlorophenyl)-3-oxo-4-phenyl-N-[4-trifluoromethyl)phenyl]-, trans-; and 1-pyrazolidinecarboxamide, N-(4-bromophenyl)-5-(2-chlorophenyl)-3-oxo-4-phenyl-, trans-.

9. A method according to claim 8 wherein an individual dose of 5 mg to 50 mg parenterally or of 5 mg to 600 mg enterally of the compound or a pharmaceutically acceptable salt thereof is administered.

* * * * *